United States Patent [19]

Bae et al.

[11] Patent Number: 5,226,902
[45] Date of Patent: Jul. 13, 1993

[54] PULSATILE DRUG DELIVERY DEVICE USING STIMULI SENSITIVE HYDROGEL

[75] Inventors: You H. Bae; Sung W. Kim, both of Salt Lake City, Utah; Lev I. Valuev, Moscow, U.S.S.R.

[73] Assignee: University of Utah, Salt Lake City, Utah

[21] Appl. No.: 737,675

[22] Filed: Jul. 30, 1991

[51] Int. Cl.⁵ .............................................. A61K 9/22
[52] U.S. Cl. ............................. 604/892.1; 604/891.1; 424/457; 424/422; 514/965
[58] Field of Search .................... 604/890.1–892.1; 424/451, 456, 457, 422, 423, 486; 514/944, 953, 962, 965

[56] References Cited

U.S. PATENT DOCUMENTS

| | | | |
|---|---|---|---|
| 3,710,795 | 1/1973 | Higuchi et al. | 604/892.1 |
| 3,994,799 | 11/1976 | Yao et al. | 604/5 |
| 4,034,756 | 7/1977 | Higuchi et al. | |
| 4,203,440 | 5/1980 | Theeuwes | 604/892.1 |
| 4,320,759 | 3/1982 | Theeuwes | |
| 4,351,337 | 9/1982 | Sidman | 604/892.1 |
| 4,503,030 | 3/1985 | Edgren et al. | |
| 4,627,850 | 12/1986 | Deters et al. | |
| 4,717,566 | 1/1988 | Eckenhoff et al. | |
| 4,743,247 | 5/1988 | Wong | |
| 4,743,248 | 5/1988 | Bartoo et al. | 604/892.1 |
| 4,783,337 | 11/1988 | Wong et al. | |
| 4,814,180 | 3/1989 | Eckenhoff et al. | |
| 4,837,111 | 6/1989 | Deters et al. | |
| 4,849,226 | 7/1989 | Gale | 424/448 |
| 4,865,598 | 9/1989 | Eckenhoff | |
| 4,871,544 | 10/1989 | Eckenhoff | |
| 4,883,667 | 11/1989 | Eckenhoff | |
| 4,948,592 | 8/1990 | Ayer et al. | |
| 4,955,881 | 9/1990 | Eckenhoff | 604/890.1 |
| 4,957,494 | 9/1990 | Wong et al. | 604/892.1 |
| 4,966,767 | 10/1990 | Eckenhoff | |
| 5,108,756 | 4/1992 | Curatolo | 424/450 |

FOREIGN PATENT DOCUMENTS

| | | | |
|---|---|---|---|
| 3629994 | 3/1988 | Fed. Rep. of Germany | 604/892.1 |
| 2173704 | 10/1986 | United Kingdom | 604/892.1 |

OTHER PUBLICATIONS

Bae et al., "Thermo-sensitive polymers as on-off switches for drug release", Makromol. Chem., Rapid Commun. 8, 481–485 (1987).

Thermally Reversible Hydrogels: II Delivery and Selective Removal of Substances from Aqueous Solutions, Journal of Controlled Release (1986 Elsevier Science Publishers B.V.) 4 (1986) 213–222.

Temperature Responsive Controlled Drug Delivery, Chapter 2, Pulsed and Self Regulated Drug Delivery, Okano et al.

Chemically Self-Regulated Drug Delivery Systems, Journal of Controlled Release 8 (1988) 111–125.

Primary Examiner—Michael H. Thaler
Assistant Examiner—Mark O. Polutta
Attorney, Agent, or Firm—Thorpe, North & Western

[57] ABSTRACT

A device for the dispensing of a biologically active material into the surrounding environment is disclosed which consists of at least one wall enclosing a compartment which contains a swollen stimuli sensitive hydrogel in which the biologically active material is entrained in solution. The hydrogel deswells or shrinks in response to contact by external physical or chemical stimuli releasing the biologically active material into the portion of the compartment previously occupied by the swollen hydrogel. The wall enclosing the compartment is rigid and contains means allowing the passage of the biologically active material from the compartment to the surrounding environment and also for transmitting the external stimuli to the swollen hydrogel in said compartment. The wall may contain orifices or be permeable to the active material and external stimuli depending upon the drug and the stimuli to be used. The hydrogel reversibly deswells, shrinks or contracts in response to stimuli, such as temperature, pH, ionic strength, glucose concentration or metabolites in the body and then reswells and reentrains active material not diffused from the compartment when the stimuli is removed. The wall may consist of one or more layers which, in combination, provide for the expeditious delivery of the active substance either through permeation through the wall or through orifices in the wall and also for the conducting of the external stimuli through the wall into the compartment to trigger the deswelling of the hydrogel.

26 Claims, 2 Drawing Sheets

PULSATILE DRUG DELIVERY DEVICE USING STIMULI SENSITIVE HYDROGEL

BACKGROUND OF THE INVENTION

This invention relates to devices which release drugs in response to environmental stimuli. More particularly, this invention relates to delivery devices containing drug laden hydrogels which deswell and release drugs from the device, hereinafter referred to as mechanical squeezing, in response to external or internal stimuli such as temperature or pH changes, or chemical reactions.

DESCRIPTION OF PRIOR ART

There have been many approaches to meet the problems of regulating the delivering of drugs or other chemicals to biological systems in the place and at the proper time and dose to achieve the desired regulatory effect. These systems depend on the utilization of physical or chemical stimuli which are a result of changes in the surrounding environment. These changes are usually of an external nature to the drug delivery system. These mechanisms respond to such stimuli or signals which include protein binding, hydrogel expanding or swelling, polymer erosion, membrane reorganization, solubility change, energy conversion, supply of activation energy for permeation, physical property changes of the materials that comprise the system, or phase transition phenomena, and the like. Examples are presented in J. Heller, Chemically self-regulated drug delivery systems, J. Control. Rel., 8, 111-125 (1988).

Additional prior art systems are described in the following patents. Higuchi et al., U.S. Pat. No. 4,034,756 is drawn to a device that essentially has two compartments, one filled with an osmotic agent or gel that swells in the presence of water and the other filled with a bioactive drug or other material. The expanding or swelling of the osmotic agent compartment or gel forces the material contained in the second compartment through an orifice. A flexible partition between the two compartments acts as a pump forcing the material in the second compartment through the orifices. Additional patents also include modified shapes and arrangements of the components. Other exemplary art, namely Deters, et al., U.S. Pat. No. 4,627,850; Eckenhoff et al., U.S. Pat. No. 4,717,566; Wong et al, U.S. Pat. No. 4,783,337; Wong, U.S. Pat. No. 4,743,247; Eckenhoff et al., U.S. Pat. No. 4,814,180; Deters et al., U.S. Pat. No. 4,837,111; Eckenhoff, U.S. Pat. No. 4,865,598; Eckenhoff, U.S. Pat. No. 4,871,544; Eckenhoff, U.S. Pat. No. 4,883,667; and Eckenhoff, U.S. Pat. No. 4,966,767 do not have the flexible partition between the two compartments. The systems disclosed in these patents rely on the expanding or swelling of the osmotic agent compartment or gel to force the drug surrounding them out through orifices or a permeable membrane. Theeuwes, U.S. Pat. No. 4,320,759 includes additional partitioning membranes. U.S. Pat. Nos. 4,871,544 and 4,966,767 include osmotic agents to enhance the expanding or swelling of the gels. Osmotic agents are also mixed with beneficial agent formulations in the second compartment in the systems taught in U.S. Pat. Nos. 4,783,337 and 4,837,111. Some patents reveal the inclusion of a density member to keep the devices in a aqueous environment. The density member is dispersed in the expandable hydrogel compartment (U.S. Pat. Nos. 4,783,337 and 4,837,111) or in separate compartments (U.S. Pat. Nos. 4,717,566 and 4,865,598) which are placed in different locations in relation to other compartments. Edgren et al., U.S. Pat. No. 4,503,030 shows pH responsive release, that is, controlled release at low pH, but dumping of all remaining agents at high pH by disintegration of the devices. This action cannot be repeated with subsequent pH changes. Ayer et al., U.S. Pat. No. 4,948,592 demonstrates a two mode release pattern, that is a one time burst releasing the beneficial agents at the beginning followed by a controlled release. This is based on the dissolution of a coating layer covering the osmotic devices, containing beneficial agents for quick release, followed by the timed sustained release of agents from the inner compartment of the device by osmotic squeezing. U.S. Pat. Nos. 4,814,180 and 4,871,544 contain temperature responsive materials in the devices disclosed. This material delivers the agent at body temperature with no release at storage temperature. At room or storage temperature, the material remains in the solid state, preventing squeezing of agents from the devices in the presence or absence of environmental water. However, at body temperature the material becomes a liquid allowing the formulation containing the beneficial agents to flow, which can then be pushed out via a passageway(s) by osmotic force. A contracting or deswelling process of hydrogels for drug delivery purposes has been reported by Hoffman et al. J. Control. Rel., 4, 213-222 (1986). A temperature sensitive hydrogel was synthesized which deswelled at elevated temperatures and swelled at low temperatures. Vitamin B12 was entrained at a low temperature and released at a higher temperature by a squeezing action. However, the overall release rate was quick and vitamin B12 was released in two steps; a fast squeezing and subsequent slow release due to a rigid surface formation on the hydrogel. It is expected that the release of entrained drug from the unprotected hydrogel at low temperatures will be unacceptably high. Therefore, this system may not be suitable for repeated pulsatile drug release by temperature modulation. The Opposite release pattern from a monolithic device Was reported by Bae et al., Makromol. Chem Rapid Commun., 8, 481-485 (1987)in which a pulsatile release was demonstrated using N-isopropylacrylamide based thermo-sensitive hydrogels (see also Hoffman et al, J. Control. Rel., 4, 213-222 (1986)). These polymers showed immediate rigid surface formation with contracting or deswelling process when the temperature was raised. This phenomenon blocks solute release from the gel matrices at an elevated temperature while allowing solute release at a low temperature. J. Kost (Ed.), *Pulsed and Self Regulated Drug Delivery*, CRC Press Inc., Boca Raton, Fl., (1990), Chapter 2, *Temperature Responsive Control Drug Delivery*, (authored by the present inventors) discloses the formation of a gel that expands or swells and contracts or deswells according to the temperature changes. This article indicates that the gel was used to entrain drug solutions but does not disclose or suggest that the gel can be contained within or used in a structured drug delivery device.

None of the prior art suggests the concept of entraining the beneficial agent in a hydrogel confined to a structured dispensing device which, when exposed to stimuli, then forces the agent by contracting or deswelling into the space within the device previously occupied by the swollen hydrogel allowing the beneficial agent to be released from the device into the surrounding environment.

OBJECTS AND BRIEF SUMMARY OF THE INVENTION

It is an object of the present invention to provide a delivery system which enables the effective delivery of drugs entrained within a hydrogel, via a squeezing mechanism, in response to external or internal, physical or chemical stimuli.

It is also an object of this invention to provide a drug delivery system from which the drug release from a hydrogel of zero or first-order kinetics is achieved in response to such stimuli.

A still further object of this invention is to provide a suitable structure for a self-regulating or externally modulated drug delivery system which gives a pulsatile release pattern from a hydrogel with a minimal lag time.

Another object of this invention is to provide a delivery system meeting the above objectives which also results in a controlled basal release of drugs from a hydrogel in the absence of stimuli or at reduced signal strength.

Yet another object is to control the triggering stimuli for the drug release from a device with the same hydrogel by changing drug loading conditions.

An additional object of this invention is to provide a stimuli responsive drug delivery system from a hydrogel enabling relatively easy drug loading and recharging when the system is exhausted.

These and other objects may be obtained by means of a dispenser device which is composed of sponge-like porous or dense hydrogel, in solid or particulate form, contained within the confines of a walled structure wherein the walls either contain dispensing orifice(s) or are permeable to the diffusion of the entrained biologically active agent or drug. Depending upon the drug and the stimuli to be used, the walls of the dispenser device may be either impermeable or permeable to chemicals that are stimuli to the swelling or expanding, or contracting or deswelling of the hydrogel. The sponge-like porous hydrogel reversibly deswells, shrinks or contracts in response to stimuli, such as temperature, pH, ionic strength, glucose concentration, metabolites in the body, or other conditions that cause the hydrogel to contract. The swollen hydrogel entrains the drug solution or formulation and the system maintains a minimal release when not subjected to stimuli that causes the hydrogel to deswell or contract. Once the hydrogel deswells or contracts in response to a stimulus, the drug in an aqueous solution is freed from the hydrogel by mechanical squeezing of the sponge-like matrix and subsequently is available for diffusion from the dispenser either through the orifice(s) in the dispenser walls or by permeation, if a permeable membrane is used. Either a minimal amount or no drug at all will be released when the hydrogel expands or reswells within the walled structure upon removal of the stimuli since undiffused drug solution is reabsorbed into the (porous) hydrogel matrix. This concept provides a drug delivery system which is reversible upon the controlled contracting or deswelling and expanding or swelling of the hydrogel in response to external stimuli.

DETAILED DESCRIPTION OF THE DRAWINGS

Figure 1:
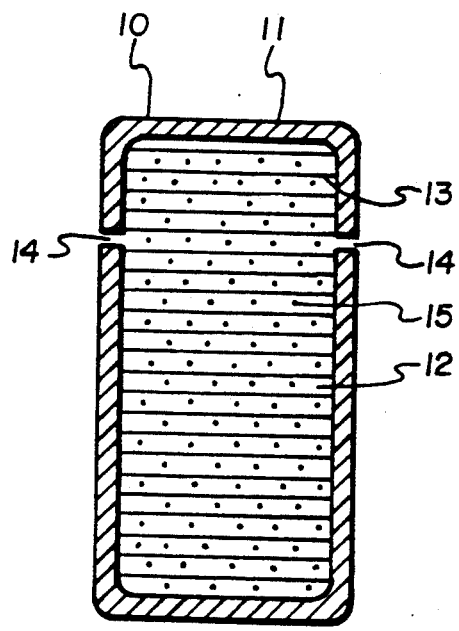
FIG. 1 shows a first embodiment consisting of a walled dispenser having an interior compartment with orifices in the walls and wherein the compartment is filled with a swollen hydrogel containing an entrained drug solution.
Figure 2:
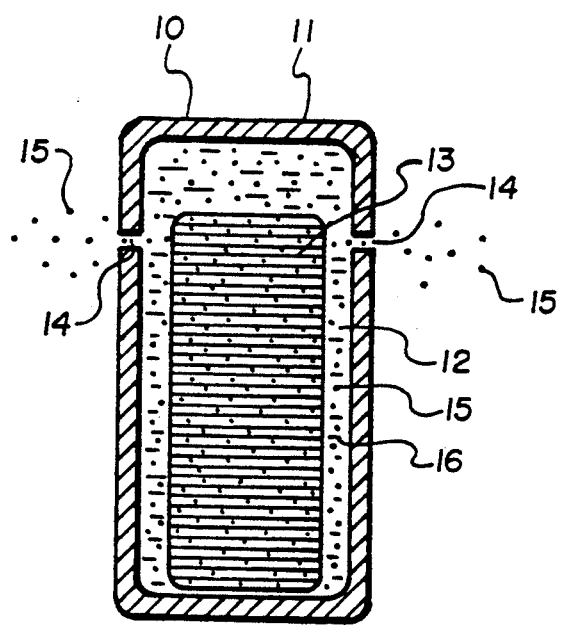
FIG. 2 shows the dispenser of FIG. 1 wherein the hydrogel is partially deswelled or contracted in response to being contacted by some form of stimuli, thereby releasing the entrained drug into the portion of the compartment space previously occupied by the swollen gel and also diffusing through the orifices in the dispenser walls into the surrounding environment.

FIGS. 1 and 2 show one embodiment of a delivery device 10 consisting of an outer wall 11, preferably constructed a material of sufficient rigidity to be self supporting. The wall defines and encloses an interior space or compartment 12. FIG. 1 shows the compartment 12 filled with a swollen hydrogel 13 containing an entrained drug solution. Hydrogel 13 is sensitive to internal or external physical or chemical stimuli such as pH or temperature changes. The walls 11 of the device contain one or more orifices 14. FIG. 1 illustrates the device a filled and ready-to-use state. The hydrogel can be continuous or particulate, porous or dense. The hydrogel must be capable of entraining a drug solution which causes the hydrogel to swell and fill compartment 12 prior to use. The degree of expanding or swelling of the hydrogel 13 is a function of external or internal, physical or chemical stimuli as is more fully described elsewhere.

FIG. 2 demonstrates drug release from the device 10 described in FIG. 1 resulting from an applied stimulus. Although not specifically shown in FIG. 1, the soluble drug 15 dissolved in a solution 16, is entrained or absorbed into the swollen hydrogel 13. The hydrogel 13 deswells, shrinks or contracts in the presence of a stimulus to only partially fill the compartment 12 as shown in FIG. 2. thereby squeezing the drug 15 in solution 16 into the portion of compartment 12 now unoccupied by the shrunken hydrogel. The drug 15 in solution 16 released from hydrogel thus resides in the compartment 12 in the space between wall 11 and deswollen hydrogel 13. The drug 15 and solution 16 is diffused from the device 10 into the surrounding media through orifices 14 or drug 15 may diffuse through wall 11 by means of permeation if the wall 11 is permeable. The wall 11 conducts the environmental stimulus to the compartment 12. The wall materials are selected based on the stimuli used and applications of the devices and are more fully described elsewhere in this specification. The orifices 14 in the device 10 are major passageways for bulk diffusion of the drug when the hydrogel 13 is deswollen with a stimulus. The size and number of the orifices 14 determines the release rate of the drug 15 into the surrounding atmosphere. The orifices 14 in the embodiment shown in FIGS. 1 or 2 can be located anywhere in the wall. When the stimulus disappears or is weakened, the drug 15 and solution 16 are reabsorbed into the hydrogel 13 to minimize or terminate the release of the drug. Although FIGS. 1 and 2 portray the device as being in the shape of a conventional capsule, the particular shape is not critical to the functioning of the device. What is essential is that the walls be constructed to conduct the applied stimuli to the hydrogel and that the drug released from the deswollen hydrogel pass through the walls by means of orifices in the walls or permeation through the wall or both into the surrounding environment.

Figure 3:
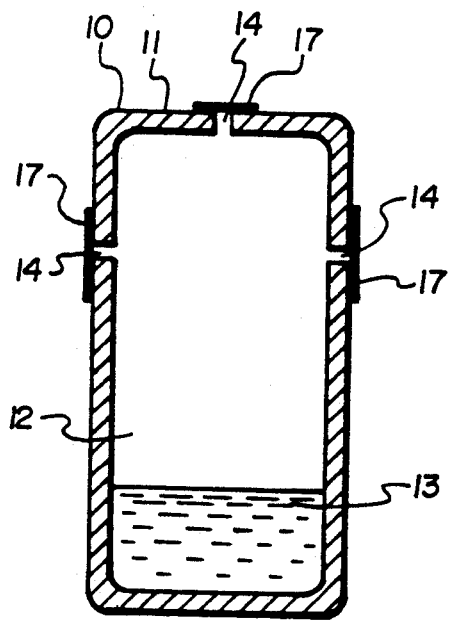
FIG. 3 shows a dispenser similar to that shown in FIG. 1 wherein the orifices are sealed and wherein the compartment contains dried hydrogel only prior to being swollen with a drug solution by the introduction of a solution through the orifices in the dispenser walls.

When the drug is unstable in an aqueous environment, the drug solution or formulation can be loaded just before use. FIG. 3 illustrates such a device. The numerals in FIG. 3 are the same as those in FIGS. 1 and 2. In FIG. 3 there is shown a dispenser device 10 containing dried hydrogel particles 13 only. The orifices 14 are sealed from the outside environment by tape or other closing means 17 on the outer surface of wall 11. The drug solution or formulation (not shown) is introduced into the compartment 12 through the one of the orifices 14, especially through the orifice shown in FIG. 3 which is located in the wall at the top after removing closing means 17 from the outer surface of wall 11. This particular orifice diameter should be large enough to allow the introduction of a drug solution or formulation into the compartment 12 using injection means. The orifice should also allow the air to be evacuated during injection. When the device 10 shown in FIG. 3 is filled with drug solution, orifice 14 should again be closed with closure means 17. However, before closing the orifice, the hydrogel should absorb the maximum amount of drug solution so as to fill compartment 12 of the device. The closure means 17 can be removed when the device is ready for use. It can be seen that the device shown in FIG. 3 will assume the same configurations and functions shown in FIGS. 1 and 2 when the hydrogel 13 is either fully swollen or is partially or fully deswollen as a result of the application of the appropriate stimuli.

Figure 4:
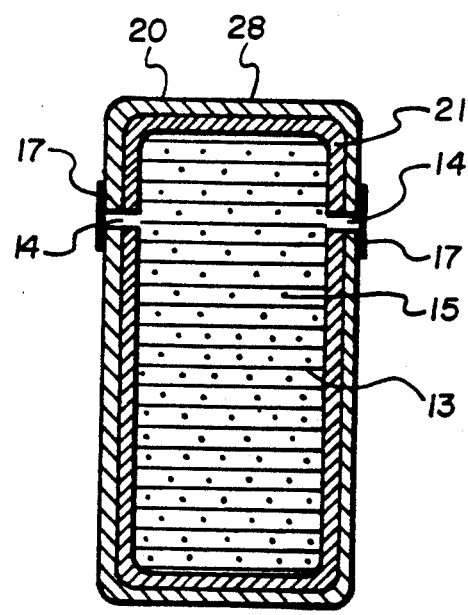
FIG. 4 shows a different embodiment consisting of a walled dispenser containing an outer permeable membrane and an inner support structure with orifices in the walls and having the dispenser compartment filled with a hydrogel swollen by an entrained drug solution.
Figure 5:
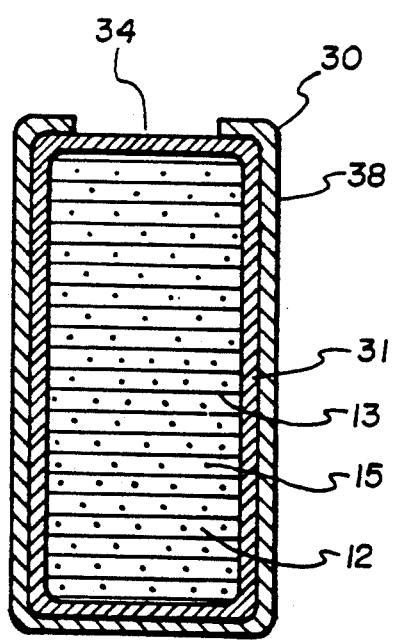
FIG. 5 shows a still different embodiment of a dispensing device consisting of a double walled structure one being a rigid outer permeable membrane partially enclosing a continuous inner permeable rigid and porous or perforated wall that allows the drug solution to diffuse from the compartment through both walls and into the environment surrounding the device.
Figure 6:
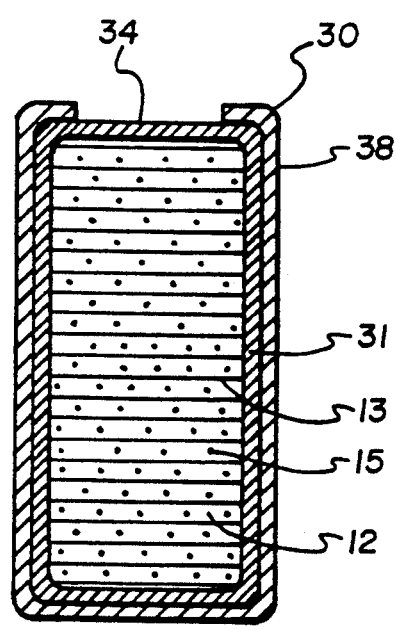
FIG. 6 shows a device similar to FIG. 5 except that the outer wall is not permeable and may or may not be rigid.

FIG. 4 illustrates a different embodiment of a delivery device 20 consisting of a rigid inner porous or perforated wall 21 covered with an outer flexible and permeable membrane wall 28. The inner wall 21 provides support allowing the device 20 to retain its original shape. Orifices 14 in each wall 21 and 28 communicate to provide a channel for the dispensing of drug from the hydrogel upon contact with the desired stimuli. In this embodiment, the stimuli can be either chemical or physical. The inner and outer walls 21 and 28 can be permeable to the stimulating molecules which permeate through the walls. Depending upon the size of the drug molecules, the walls may also be permeable to the dispensing of the drug. In other words, drug may be delivered to the surrounding environment both through the communicating orifices 14 in the walls and by permeation through walls 21 and 28. FIGS. 5 and 6 illustrate a still different embodiment consisting of a delivery device 30 having inner and outer walls neither of which have orifices through which the drug is to be discharged into the environment. The device 30 illustrated in FIGS. 5 and 6 has an inner wall 31 made of a rigid porous or perforated material which is permeable to the drug 15 and drug solution 16. An Outer membrane wall 38 only partially covers the inner wall 31 and is shown in both FIGS. 5 and 6 as leaving a wall opening 34 at the top of the device. The uncovered portion of inner wall 31 defined by opening 34 in outer wall 38 can be used as a passageway for drug release in the place of orifices. When hydrogel 13 is in the form of small particles, this type of structure prevents any possible leakage of such particles from the device.

In the FIG. 5 embodiment, the outer wall 38 is permeable, either to chemical stimuli entering the device to trigger the release of drug or to the dispensing of drug through the outer wall. This embodiment is particularly adapted for use in a system for the utilization of chemical stimuli with the release of drug through the inner wall in the area of opening 34 in the outer wall. In this embodiment, the outer wall 38 can be either flexible and non-supporting or rigid and supporting.

The embodiment of FIG. 6 is similar in all respects to FIG. 5 except that the outer wall or membrane 38 is not permeable. Provided the inner wall 31 is structurally self-supporting, the outer impermeable wall 38 may be either flexible or rigid. In either event the dispensing of drug will be through the inner wall 31 in the area of the opening 34 in the outer wall. This embodiment may be more readily adaptable to physical stimuli, such as temperature, than chemical. However, inner membrane may still be permeable to chemical stimuli which penetrates the inner wall through opening 34 in the outer wall.

DETAILED DESCRIPTION OF THE INVENTION

As can be seen from the above description of the various embodiments shown in the drawings, the invention is directed to devices made up of impermeable or permeable enveloping walls having an interior space or compartment filled with sponge-like porous or dense hydrogel o hydrogel particles which entrain drug solutions or formulations. By "enveloping walls" is meant any structure having an inner compartment space surrounded by walls. These may be in the form of hollow spheres, boxes, rods or any other number of configurations. For the sake of simplicity, these will generally be referred to throughout this disclosure as "capsules". However, the term "capsule" is not to be limited to the shape of the conventional gelatin capsule utilized for the dispensing of medicines. Also, the term, "wall(s)" may be used to define a single continuous wall enclosing a compartment or a discontinuous wall, such as is found in a conventional capsule wherein there are two sections one of which is telescoped into the other to form a compartment. Further, a capsule may consist of a lower hollow section onto which is fitted a top to complete the enclosed compartment.

The devices of this invention can utilize, in the compartment thereof, any hydrogel which swells to entrain an aqueous drug solution and which deswells or contracts in response to external or internal, physical or chemical stimuli to release or squeeze out the drug solution. The invention is not drawn to any novel hydrogels or class of novel hydrogels. There are various suitable hydrogels already taught in the prior art which react appropriately to drug entrainment and deswell or contract in response to contact by appropriate chemical and/or physical stimuli. Some of these hydrogels are referenced above. However, there also may now exist, or be developed in the future, other hydrogels which can also be utilized in this invention. Therefore, the invention is to be limited only by the functionality of the hydrogels and is inclusive of all hydrogels which meet the parameters given above. For example, N-isopropylacrylamide based copolymers or interpenetrating polymer networks can be used as temperature sensitive hydrogels and crosslinked polyelectrolytes as pH sensitive hydrogels. These hydrogels deswell or contract as a result of increasing temperature or variations in the environmental pH. Typical temperature sensitive hydrogels are disclosed in Bae, et al. Temperature Dependence of Swelling of Crosslinked poly(N,N-alkyl Substituted Acrylamide) in Water, *J. Polym. Sci.: Part B: Polym. Phys.*, 28 (1990) 923; Y. H. Bae, et al., A New Thermo-sensitive Hydrogel: Interpenetrating Polymer Networks from N-acryloylpyrrolidine and poly(oxyethylene), *Makromol. Chem., Rapid Commun.*, 9 (1988), 185; and Ilmain, et al., Volume Transition in a Gel Driven by Hydrogen Bonding, *Nature*, 349 (1991) 400. pH sensitive hydrogels are disclosed in Brannon et al., The Swelling Behavior of pH Sensitive Hydrogels. *Proceed. Intern. Symp. Control. Rel. Bioact. Mater.*, 15 (1988) 28; and Siegel et al., pH-Dependent Equilibrium Swelling Properties of Hydrophobic Polyelectrolyte Hydrogels, *Macromolecules*, 21 (1988) 667.Photo-sensitive hydrogels are described in Ishihara,et al., Photo Induced Swelling Control of Amphophilic Azoaromatic Polymer Membrane, *J. Polym. Sci.: Polym. Chem. Ed.*, 22 (1984) 121; Sunamoto, et al., Liposomal Membranes, 13. Transport of an Amino Acid Across Liposomal Bilayer as Mediated by Phoresponsive Carrier, *JACS*, 104 (1982) 5502; Irie, et al., Photo Responsive Polymers, 8. Reversible Photo Stimulated Dilation of Polyacrylamide Gels Having Triphenylmethane Leuco Derivatives, Macromolecules, 19 (1986) 2477; Marada, et al., Photo Induced Phase Transition of Gels, *Macromolecules*, 23 (1990) 1517; Suzuki, et al., Phase Transition in Polymer Gels Induced by Visible Light, *Nature*, 346 (1990) 345. Glucose sensitive hydrogels are illustrated in Kost, et al., Glucose-Sensitive Membranes Containing Glucose Oxidase: Activity, Swelling and Permeability Study, *J. Biomed. Mater. Res.*, 19 (1985) 1117; Albin, et al., Theoretical and Experimental Studies of Glucose Sensitive Membranes, *J. Control. Rel.*, 6 (1987) 267; Ishihara, et al, Glucose Induced Permeation Control of Insulin Through a Complex Membrane Sensitivity of Immobilized Glucose Oxidase and a Poly(amine), *Polymer J.*, 16 (1984) 625.

Temperature sensitive hydrogels, which are crosslinked homopolymers or copolymers, may be made from the following monomers: N-isopropylacrylamide, N,N-diethylacrylamide, acryloylpiperidine, N-ethylmethacrylamide N-n-propylacrylamide and N-(3'-methoxypropyl)acrylamide, preferably N-isopropylacrylamide, N,N'-diethylacrylamide and N-n-propylacrylamide. A crosslinking agent is required for gel formation. Typical classes of crosslinking agents include (1) di-,tri-, or tetraacrylates such as bisphenol-A diacrylate, 1,3-butanediol diacrylate, 1,4-butanediol diacrylate, 1,10-decanediol diacrylate, diethylene glycol diacrylate, 1,6-hexamethylene diacrylate, pentaerithritol tetraacrylate, pentaerithriol triacrylate, p-phenylene diacrylate, tetraethylene glycol diacrylate, triethylene glycol diacrylate, 1,1,1-trimethylolethane triacrylate, and 1,1,1-trimethylolpropane triacrylate; (2) di-, tri-, or tetramethacrylates such as bisphenol-A dimethacrylate, bisphenol-A-bis(hydroxyprophyl) methacrylate, 1,3-butanediol dimethacrylate, 1,4-butanediol dimethacrylate, crotyl methacrylate, 1,4-cyclohexanediol dimethacrylate, 1,10-decanediol dimethacrylate, diethylene glycol dimethacrylate, 2,2,-dimethylpropanediol dimethacrylate, glyceryl trimethacrylate, hydrogenated bisphenol-A dimethacrylate, pentaerithritol tetramethacrylate, tetraethylene glycol dimethacrylate, triethylene glycol dimethacrylate, and 1,1,1-trimethylolpropane trimethacrylate; (3) chemicals containing diallyl groups such as N,N-Diallylacrylamide, diallyl diglycol carbonate, diallyl fumarate, diallyl maleate, diallyl phthalate, N,N'-diallyltartardiamide, and diallylterephthalate; (4) chemicals having divinyl groups such as divinylbenzene; and, (5) others materials such as 4-methacryloxyethyl trimellitate anhydride and N,N'-methylene bisacrylamide. The resulting gel will swell at lower temperature and deswell at higher temperature. Preferred crosslinking agents are water soluble or slightly water soluble and are miscible With monomers.

pH sensitive hydrogels may be made by polymerizing the following monomeric unsaturated acids: 2-acetamidoacrylic acid, acrylic acid, cis-aconitic acid, trans-aconitic acid, allylacetic acid, 2-allylphenoxyacetic acid, β-benzoacrylic acid, 2-chloroacrylic acid, crotonic acid, N,N-di-n-butylmaleamic acid, fumaric acid, N,N-diethylmaleamic acid, dihydroxymaleic acid, itaconic acid, 3,3-dimethylacrylic acid, N-ethylmaleamic acid, trans-2-hexenoic acid, trans-3-hexenoic acid, methacrylic acid, maleic acid, 5-norbornene-2-acrylic acid, trans-2-pentenoic acid, 1,4-phenylenediacrylic acid, N-phenylmaleamic acid, vinylacetic acid, 2,4-hexadienonic acid, 4-vinylbenzoic acid, and 2-vinylpropionic acid pH sensitive hydrogels may also be made by polymerizing polymerizable bases containing amino or amine groups such as: allylamine, allycyclohexamine, allyldiethylamine, allyldimethylamine, allylethylamine 1,4-bis(diallylamino)butene-2, 1,3-bis(diallylamino)propane, bis(diallylamino)methane, t-butylaminoethyl methacrylate, diallylamine, N,N-diallylaminoacetonitrile, 2-N,N-diallylaminoethylamine, diallylmethylamine, diallyl-2-ethylhexylamine, N,N-diallylethanolamine, diallylaminopropionitrile, N,N-dimethallylamine, N,N-dimethyllallylamine, N,N-dimethylaminoethyl acrylate, N,N-dimethylaminoethyl methacrylate, N,N-dimethylaminopropyl acrylamide, N,N-dimethylaminopropyl methacrylamide, N,N-diethylaminoethylacrylate, and N,N-diethylaminoethylmethacrylate. A crosslinking agent such as is used for the formation of temperature sensitive gels is required for gel formation. The resulting gels from monomeric acids will swell at higher pH values and deswell at lower pH values. The resulting gels from monomeric bases will show an opposite swelling behavior.

Ionic sensitive hydrogels are made in the same manner as the pH sensitive hydrogels.

Glucose sensitive hydrogels are made by using glucose oxidase, an enzyme which converts glucose to gluconic acid and peroxide. As used herein glucose sensitive hydrogels are glucose oxidase immobilized pH sensitive hydrogels made from acid monomers, listed above as pH sensitive components, plus 4-carboxy styrene (see Broos et al., *J. Chem. Ed.* 55 (1978) 813). These gels deswell in the presence of glucose.

The walls of the impermeable capsule can be formulated from any inert material which has minimal volume change with a given stimulus. The capsule materials must have a capacity to conduct a given stimulus from outside environment to the compartment or vice versa. The capsule materials must have a minimal interaction with the entrained drug solution or formulation and should be inert to an aqueous environment. The materials required for an impermeable capsule include natural or synthetic polymers, ceramic or metallic materials. Surface modified plastics to minimize interactions with drug formulations can also be used.

When the hydrogel is reactive to chemical signals, the capsule membrane can be made of impermeable or permeable materials. With the impermeable membrane, signal molecules can only enter through the orifice(s) in the capsule walls. In this case, the response of drug release to signal changes may be delayed if the flux rate for the signal molecules through the orifice(s) is not fast enough. The flux rate can be more precisely controlled by a permeable membrane having a certain molecular cutoff, which allows permeation of signal molecules and water, but is not permeable to the drug molecules entrapped by the hydrogel. If a basal release of drug molecules is required, the permeable membrane allows entry of signal molecules and the outward diffusion or permeation of drug molecules. When the permeable material (membrane) is so flexible that the capsule can not maintain its original shape, porous or perforated rigid materials can be used as supporting structures in the construction of the capsule as is demonstrated in the devices shown in FIGS. 4, 5 and 6. Then a flexible semi-permeable membrane can be overlaid on the supporting materials as is shown in FIGS. 4 and 5.

Semi-permeable polymer membranes for use in the pH sensitive device which allow H+ and OH- ions to diffuse through the membranes by osmosis and reverse osmosis are formed typically from cellulose derivatives, such as cellulose esters, cellulose ethers, cellulose ester-ethers, cellulose acrylate, cellulose diacrylate, cellulose triacrylate, cellulose acetate, cellulose diacetate, cellulose triacetate, hydroxypropyl methylcellulose, mixtures thereof. (A more detailed description of suitable semipermeable membranes is found in U.S. Pat. 4,966,767, col. 6, line 16 to col. 7, line 33.)

The permeable membranes, such as those useful in the glucose sensitive devices, have a certain molecular Weight cut-off. These membranes allow for free diffusion of signal molecules, such as glucose, and for basal diffusion of beneficial drugs. Such polymers are known as dialysis membranes, such as cellulose acetate, regenerated cellulose, polysulfone, and polymethylmethacrylate.

Inclusive of other polymers that allow diffusion of signal molecules and basal diffusion of beneficial drugs are (1) ultra filtration porous membranes such as made of ethylene vinylacetate, polypropylene, polyvinylidene difluoride, and polycarbonate; (2) hydrogel membranes having appropriate water content for diffusion of signal molecules and drugs, e.g. those composed of hydrophilic polymers such as polyhydroxyethyl methacrylate, polyvinylpyrrolidone, polyacrylamide, and alkyl derivatives thereof; and (3) copolymers of (a) water soluble monomers, such as vinylpyrrolidone, hydroxyethylmethacrylate, acrylamide, alkyl derivatives of acrylamide (N-ethylacrylamide, N,N-dimethylacrylamide, Nmethylacylamide, N,N-diethylacrylamide and the like), acrylic acid, methacrylic acid, and the like and (b) water insoluble monomer such as styrene, alkylmethacrylates, and alkylacrylates.

The devices of the invention can be used for rectal delivery of antipyretic drugs and other pharmacologically active agents. For the treatment of symptoms/diseases where a fever is a present, antipyretic drugs can be released from devices containing temperature sensitive hydrogels in response to the increase in body temperature (above normal body temperature >38° C.) and the fever can be controlled automatically. Other therapeutic agents can also be released in response to the change in body temperature caused by diseases, such as in malaria.

This approach can be used for insulin dependent diabetic patients by implantation of the device containing glucose sensitive gels in the peritoneal cavity. Glucose oxidase converts glucose to gluconic acid resulting in an acidic environment. This characteristic of the gel can be utilized in making glucose sensitive gels in which glucose oxidase is immobilized in polybase which swells upon contact with glucose. These devices utilize crosslinked polyacid gels containing glucose oxidase. The polyacid will then shrink in the presence of glucose, resulting in insulin release.

Similar devices for self-regulating drug delivery can be made utilizing appropriate signal molecules and hydrogels responding to the signal.

Using pH sensitive gels which deswell at physiological pH but swell in stomach pH, these devices can be fashioned to orally deliver labile agents into the acidic environment.

The compartment volume and shape of the device will depend on the actual use. The compartment volume will range from a few microliters to several hundred milliliters or larger. The shape of the device is governed by the eventual use of the device and any shape with a certain compartment volume will be acceptable as long as it can be filled with the porous hydrogel or hydrogel particles. The preferred shapes are cylindrical, disc, or slight modifications of these shapes such as bullet for pharmaceutical applications.

Devices shown in FIGS. 1, 2 and 3 are made by drilling a hole(s) on the impermeable rigid capsule wall. To make double wall devices, presented in FIGS. 4, 5, and 6, permeable or semipermeable tubing can be used. A dialysis tubing with a hole or holes is inserted into a fabricated capsule and both ends are sealed by glue or other means of closing the ends. The peripheral edge of the hole or holes is glued making tight contact with the capsule wall insuring precise control of drug flux.

The dimension of the device dependent upon a specific application. For example, the size and shape of the device is similar to suppositories in the market for the rectal delivery of antipyretic drugs. For insulin delivery, the volume ranges from 5 ml to 200 ml. The size and shape of the device can vary in response to the actual application needs (i.e., cylinder or disk types). In actual application the preferred size and configuration will be obvious to the skilled practitioner.

One or more orifices can be located anywhere on the capsule walls. The diameter of each orifice can range from a micrometer to several millimeters. The number and the diameter of the orifices determine basal release and the rate of release in relationship to a given signal strength. The orifices should be placed where they contact the inner hydrogel and do not interfere with the filling procedure.

To prevent the possibility of leaking hydrogel particles into the environment the orifices can be replaced by a passageway which communicates with a permeable membrane as illustrated in FIGS. 5 and 6. Only a single passageway 34 is shown in these figures; however, the number, location and size of these passageways can be varied according to the use of the device.

The (porous) swellable hydrogel which expands when acted upon by a given stimulus can be synthesized by solution polymerization and crosslinking. In order to generate a porous structure for the hydrogel, polymerization should be carried in a solvent which dissolves the monomer but is not a solvent for the crosslinked polymer. The resulting crosslinked polymers have a porous structure. However, the detailed synthetic conditions and procedures for the manufacturing of the (porous) hydrogel may depend upon monomer and polymer properties.

Hydrogel particles can be produced by suspension polymerization or breaking large polymer pieces into smaller pieces. The size of polymer particles in a deswollen or contracted state should be bigger than the orifice diameter of the drug delivery device to prevent the particles from leaking. The hydrogels are materials Which swell or deswell in response to pH, temperature, chemical reactions, concentration of chemical or biological substances, enzyme mediated processes and other stimuli.

The drugs used in the device should be soluble in an aqueous solution and diffusible in the aqueous media surrounding the device. The type and size of the drug is not limited. The device delivers drugs ranging in size from several angstroms to a few microns in diameter.

The invention is not limited to the use of any type or class of drug or other pharmaceutical agent as long as it is functional for use in the gels described. Acetaminophen, allopurinol, aspirin, magnesium salicylate, phenacetin, sodium salicylate, diflunisal, ibuprofen, indomethacin, naproxen, naproxen sodium, oxyphenbutazone, phenylbutazone and tolmetin sodium are examples of antipyretic drugs that can be used in connection with the temperature sensitive devices. Insulin is used with the glucose sensitive device. Other drugs suitable for use in these devices are listed in standard publications of which *Remington's Pharmaceutical Sciences, The Merck Index or Physicians Desk Reference*. The functionality of any given drug may be readily determined by those skilled in the art.

The conditions for loading the hydrogel with drugs may determine the triggering signal strength which causes gel contracting or deswelling, followed by drug release. When the degree of swelling of a hydrogel is a continuous function of the signal strength, the drug can be loaded into the hydrogel at a given signal strength. This signal strength is a critical point for drug release. When a stronger signal strength causes contracting or deswelling of the hydrogel in relationship to the signal strength of the loading condition, the enhanced drug release occurs, while if a weaker signal strength causes more swelling than the loading condition, the release is at a zero or a minimal level. Therefore, the critical point can be varied with the same hydrogel depending on the loading condition.

These devices can be used in a variety of applications, i.e., orally, rectally, vaginally, or implanted depending on the conditions to be treated. For example, capsules can be made for oral ingestion that release anti-ulcer drugs in response to the increase in acidity the stomach and then are dissolved by the high pH of the intestines. Additionally, suppositories can be made, to be inserted in the rectum or vagina for uniform release of a drug, without fear of excess dosage, to control fever or alleviate other symptoms. Implantable capsules can be formed, as set forth above, that are implanted under the skin or in the peritoneal cavity, which when exposed to high glucose levels release insulin as needed for the control of diabetes.

The examples which follow are representative of the invention but are not to be considered as limitations thereof.

EXAMPLE 1

A device for pulsatile release of a drug is fabricated from 1 mm thick impermeable polypropylene in capsular form to define an interior space Or compartment. The capsule is cylindrical and is 5.2 cm in height, has a 1.1 cm inside diameter and is closed at the top by a friction fitting snap top having one 1.3 mm diameter opening in the center. Instead of fabricating the capsule from polypropylene a similar device can be made using any kind of inert rigid materials which do not swell in an aqueous environment, i.e. plastics, sheet metals and ceramics. For example, plastics such as polyethylene, polystyrene, polycarbonate, polyvinyl chloride, and polyesters may be utilized.

EXAMPLE 2

Several crosslinked poly(N-isopropylacrylamides) were synthesized as temperature sensitive hydrogels suitable for use in the present invention. N-isopropylacrylamide (1 gram) with N,N'-methylenbisacrylamide (0.02 to 0.1 g) was dissolved in water to make 5 ml volume. Polymerization was initiated in the solution by ammonium persulfate (1 mg) and N,N,N',N'-tetramethylethylene diamine (10 $\mu$g). The polymerization was performed in ice water for one hour. Each gel obtained was soaked in distilled water to remove unreacted compound and sol fraction. To exemplify the degree of swelling of these gels as a function of temperature, a hydrogel formed by the polymerization of one gram of N-isopropylacrylamide and 0.1 gram of N,N'-methylenebisacrylamide was utilized. The gel was first freeze dried, broken into small pieces and was then allowed to equilibrate at various temperatures using an aqueous acetaminophen solution at a concentration of 1 mg/ml. The degree of swelling, given in Table 1, is the ratio of $V_s/V_p$ where $V_s$ is the absorbed water volume and $V_p$ is the dried polymer volume:

TABLE 1

| Temperature (°C.) | $V_s/V_p$ |
|---|---|
| 10 | 13.6 |
| 20 | 11.3 |
| 26 | 9.0 |
| 28 | 8.1 |
| 30 | 6.0 |
| 32 | 5.3 |
| 32.6 | 4.1 |
| 33 | 1.9 |
| 34 | 1.7 |
| 40 | 1.5 |

These data quite clearly show the shrinkage of the polymer as a function of rising temperature.

EXAMPLE 3

Freeze dried hydrogel pieces prepared as in Example 2 were equilibrated in aqueous acetaminophenol solution at 1 mg/ml concentration at room temperature. The swollen gel pieces were placed in the compartment of the device described in Example 1 and monitored for acetaminophen release over an extended period of time as a function of temperature modulation. Release data are presented in Table 2.

TABLE 2

| Release Rate (mg/min) | Temperature (°C.) | Elapsed Time (hours) |
|---|---|---|
| n.d.* | 20 | 1.0 |
| n.d. | 20 | 21.2 |
| n.d. | 30 | 25.6 |
| n.d. | 31 | 30.4 |
| 0.6 | 31 | 30.8 |
| 1.0 | 31 | 31.2 |
| 1.0 | 31 | 32.0 |
| 1.0 | 33 | 46.0 |
| 2.4 | 33 | 46.4 |
| 3.1 | 33 | 47.0 |
| 3.8 | 33 | 47.6 |
| 4.4 | 33 | 48.4 |
| 4.8 | 33 | 50.0 |
| 4.8 | 30 | 52.3 |
| n.d. | 30 | 53.6 |
| n.d. | 33 | 69.0 |
| 2.9 | 33 | 70.0 |
| 6.0 | 33 | 71.8 |
| 6.0 | 20 | 74.0 |
| n.d. | 20 | 75.2 |

*not detectable by UV

These results clearly show that release rate is responsive to temperature modulation with release rates going up as a function temperature increase and dropping as the temperature is lowered.

EXAMPLE 4

A temperature sensitive copolymer consisting of acrylic acid (12 mole %), and N-isopropylacrylamide (88 mole %) was synthesized following the same procedure as in Example 2. The added amount of N,N'-methylenebisacrylamide was 4.2 mole % of the total monomers. The hydrogel polymer was recovered and freeze dried for future use.

EXAMPLE 5

The same procedure utilized in Example 3 was repeated using the hydrogel obtained in Example 4 and was loaded at 36° C. instead of at room temperature.

As in Example 3, acetaminophen release was monitored as a function of temperature modulation over a period of time. These results are reported in Table 3.

TABLE 3

| Release Rate (μg/hr) | Temperature (°C.) | Elapsed Time (hours) |
|---|---|---|
| — | 30 | 0.0 |
| n.d.* | — | 0.1 |
| — | 34 | 0.2 |
| n.d. | — | 0.3 |
| — | 36 | 0.5 |
| 140 | — | 0.8 |
| — | 38 | 1.0 |
| 120 | — | 1.1 |
| — | 40 | 1.3 |
| 120 | — | 1.5 |
| — | 44 | 2.0 |
| 110 | — | 2.5 |
| — | 42 | 3.0 |
| 110 | — | 3.3 |
| — | 40 | 3.5 |
| 60 | — | 3.8 |
| — | 38 | 4.0 |
| 60 | — | 4.3 |
| — | 36 | 4.5 |
| 20 | — | 4.8 |
| — | 34 | 5.0 |
| n.d. | — | 5.3 |
| — | 36 | 5.5 |
| 130 | — | 5.8 |
| — | 40 | 6.0 |
| 65 | — | 6.5 |
| — | 40 | 7.0 |
| 40 | — | 7.3 |
| — | 36 | 7.5 |
| n.d. | — | 7.8 |

*not detectable by UV

These results again show that release rate is responsive to temperature modulation with release rates being maximum at about the loading temperature of 36° C.

EXAMPLE 6

Crosslinked pH sensitive poly(acrylic acid) hydrogel was prepared following the procedure essentially as described in Example 2. A mixture of 0.5 ml of acrylic acid and 0.042 gram of N,N'-methylene bisacrylamide was dissolved in 4.5 ml of carbonate buffer (pH 8). This solution was polymerized by the same amount of redox initiator as in Example 2. After purification, the freeze-dried hydrogel pieces were placed in the compartment of the device described in Example 1, followed by the addition of aqueous insulin solution at a concentration of 1 mg/ml. After equilibration the device was closed with the snap fitting top. The rate of insulin release by varying the pH is illustrated in Table 4.

TABLE 4

| Release Rate (mg/min) | pH | Elapsed Time (hours) |
|---|---|---|
| n.d.* | 8.0 | 3.2 |
| 0.4 | 6.0 | 8.0 |
| n.d. | 5.0 | 14.0 |
| 0.5 | 5.0 | 31.0 |
| 1.1 | 4.4 | 46.5 |
| 5.4 | 4.4 | 48.0 |
| 5.4 | 6.0 | 51.0 |
| 1.0 | 6.0 | 52.0 |
| 1.0 | 6.0 | 56.2 |

*not detectible by UV

These results demonstrate that, at the lower pH ranges, the release rate intensifies and that, when pH is raised, the release rate is diminished.

While the invention has been described and illustrated with reference to certain preferred embodiments thereof, those skilled in the art will appreciate that various modifications, changes, omissions, and substitutions can be made without departing from the spirit of the invention. It is intended, therefore, that the invention be limited only by the scope of the following claims.

We claim:

1. A device for the dispensing of a biologically active material into a surrounding environment by bulk diffusion comprising a wall defining an interior compartment; said compartment containing a swollen stimuli sensitive hydrogel in which the biologically active material is entrained in solution which hydrogel deswells in response to contact by external stimuli thereby releasing said biologically active material into said compartment of outward diffusion; said wall being rigid and containing means allowing the passage of said biologically active material released from said deswollen hydrogel from said compartment by outward diffusion to said surrounding environment and also containing means for transmitting said external stimuli from said outside environment to said swollen hydrogel in said compartment.

2. The device of claim 1 wherein the biologically active material is squeezed from the hydrogel as said hydrogel deswells causing said biologically active material to enter into the portion of the compartment previously occupied by the deswollen hydrogel thereby allowing said biologically active substance to be released through said wall and into the environment surrounding said device.

3. The device of claim 1 wherein said wall contains orifices and wherein the means for allowing the passage of said biologically active material from said compartment to said surrounding environment is through said orifices.

4. The device of claim 3 wherein said orifices are sized to prevent the passage of deswollen hydrogel from said compartment into the surrounding environment.

5. The device of claim 4 wherein said wall is made from a material which is impermeable to the passage of said biologically active substance and chemical stimuli.

6. The device of claim 5 wherein said material is selected from the group consisting of natural polymers, synthetic polymers, ceramics and metallic materials.

7. The device of claim 4 wherein said wall made from a material which is impermeable to the passage of said biologically active substance but is permeable to the passage of chemical stimuli.

8. The device of claim 7 wherein the chemical stimuli is change in pH and said wall is made from a material which is permeable to chemical agents affecting hydrogen ion concentration.

9. The device of claim 8 wherein said wall is made from a material selected from the group consisting of cellulose esters, cellulose ethers, cellulose ester-ethers, cellulose acrylate, cellulose diacrylate, cellulose triacrylate, cellulose acetate, cellulose diacetate, cellulose triacetate, hydroxypropyl methylcellulose, and mixtures thereof.

10. The device of claim 2 wherein said wall is permeable to both diffusion of the biologically active material and physical and chemical stimuli thereby allowing outward diffusion of the biologically active material from said compartment into the surrounding environment and inward diffusion of chemical stimuli through said wall into said compartment.

11. The device of claim 10 wherein said wall is constructed of a material selected from the group consisting of dialysis membrane materials.

12. The device of claim 11 wherein said dialysis membrane materials are selected from the group consisting of cellulose acetate, regenerated cellulose, polysulfone, and polymethylmethacrylate.

13. The device of claim 12 wherein the chemical stimuli is glucose concentration and said wall is permeable to the passage of glucose and insulin or an insulin substitute.

14. The device of claim 10 wherein said wall is constructed of materials that allow diffusion of signal molecules and basal diffusion of beneficial drugs selected from the group consisting of ultra filtration porous polymer membranes; hydrogel membranes having appropriate water content for diffusion of signal molecules and drugs; and copolymers of water soluble monomer and water insoluble monomers.

15. The device of claim 14 wherein said material is an ultra filtration porous polymer membrane.

16. The device of claim 15 wherein the, porous polymer membrane is a member selected from the group consisting of ethylene vinylacetate, polypropylene, polyvinylidene difluoride, and polycarbonate.

17. The device of claim 14 wherein said material is a hydrogel membrane having appropriate Water content for diffusion of signal molecules and drugs.

18. The device of claim 17 wherein said hydrogel membrane is a hydrophilic polymer selected from the group consisting of polyhydroxyethyl methacrylate, polyvinylpyrrolidone, polyacrylamide and alkyl derivatives thereof.

19. The device of claim 14 wherein said material is a copolymer of a water soluble monomer and a water insoluble monomer.

20. The device of claim 19 wherein said water soluble monomer is a member selected from the group consisting of vinylpyrrolidone, hydroxyethylmethacrylate, acrylamide, alkyl derivatives of acrylamide (N-ethylacrylamide, N,N-dimethylacrylamide, N-methylacylamide, N,N-diethylacrylamide and the like), acrylic acid, methacrylic acid, and the like, and said water insoluble monomer is a member selected from the group consisting of styrene, alkylmethacrylates, and alkylacrylates.

21. The device of claim 10 wherein said wall is at least partially surrounded by a second outer wall wherein said outer wall contains at least one opening exposing said wall to the surrounding environment providing a passageway for the diffusion of said biologically active substance and said chemical stimuli.

22. The device of claim 21 wherein said outer wall is a flexible membrane permeable to chemical stimuli but impermeable to the biologically active substance.

23. The device of claim 21 wherein said outer wall is a flexible membrane impermeable to both chemical stimuli and the biologically active substance.

24. The device of claim 21 wherein said outer wall is a flexible membrane permeable to both chemical stimuli and the biologically active substance.

25. The device of claim 2 wherein said wall is a structured porous support said wall being surrounded by a second flexible membrane outer wall said wall and outer wall both containing communicating apertures which provide a channel for the delivery of said biologically active substance from said compartment to said surrounding environment.

26. The device of claim 25 wherein said outer wall is a flexible membrane permeable to chemical stimuli but impermeable to the biologically active substance.

* * * * *